United States Patent [19]
Hanifl

[11] 3,961,529
[45] June 8, 1976

[54] URINE METERING AND COLLECTION SYSTEM

[75] Inventor: Paul Hanifl, Warwick, R.I.

[73] Assignee: International Paper Company, New York, N.Y.

[22] Filed: Aug. 9, 1973

[21] Appl. No.: 387,011

[52] U.S. Cl. .................................. 73/219; 73/427; 128/2 F
[51] Int. Cl.[2] ...................... A61B 5/00; G01F 11/28
[58] Field of Search ............ 73/426, 427, 223, 422, 73/202, 219; 128/2 F, 295, 349 R, 214.4, DIG. 24, 275; 4/110

[56] References Cited
UNITED STATES PATENTS

| | | | |
|---|---|---|---|
| 3,345,980 | 10/1967 | Coanda | 128/2 F |
| 3,362,400 | 1/1968 | Bella | 128/2 F |
| 3,599,637 | 8/1971 | Schwartz | 128/214.4 |
| 3,661,143 | 5/1972 | Henkin | 128/2 F |
| 3,683,894 | 8/1972 | Villari | 128/2 F |
| 3,888,236 | 6/1975 | Marx | 128/2 F |

FOREIGN PATENTS OR APPLICATIONS

| | | | |
|---|---|---|---|
| 53,188 | 9/1942 | Netherlands | 73/427 |

*Primary Examiner*—S. Clement Swisher
*Attorney, Agent, or Firm*—Finnegan, Henderson, Farabow & Garrett

[57] ABSTRACT

A urine metering and collection system is disclosed which includes a relatively stiff integral head member having a volume calibrated chamber with sidewalls continuously converging downwardly towards each other such that each horizontal section of the chamber has a smaller volume per unit of height than does the next adjacent upper horizontal section throughout a major portion of the length of the chamber, an outlet passageway adjacent the bottom of the chamber; an inlet passageway adjacent the top of the chamber, an overflow passageway having one end in fluid-flow communication with the top of the chamber and an air vent communicating with the chamber; a collection bag fixedly secured to the head member below the chamber and in flow communication with the outlet overflow passageway, which also serves as a vent for the bag, and including an opening and a drain tube; and conduit means for placing the chamber outlet passageway and the collection bag opening in flow communication, the conduit means preferably having a three position valve including one position for sampling fluid in the metering chamber.

10 Claims, 2 Drawing Figures

3,961,529

URINE METERING AND COLLECTION SYSTEM

BACKGROUND

This invention relates to a closed system for collecting and measuring the volume of urine output of patients and, more particularly, to a system which provides improved metering and structural rigidity.

Urine metering and collection systems are a valuable medical tool and are commonly used for medical examination and diagnosis. It is common to employ a urinary drainage tube to connect a catheter to a collection bag or a metering device. Many existing devices do not provide sufficiently accurate measurement of urinary volume, especially when the volume output is small. To overcome this problem metering devices have been designed with two chambers of different diameters, the smaller diameter chamber providing relatively good accuracy for small volume measurement and the larger diameter chamber providing relatively accurate measurement for large volume output. however, because of the change in diameter accurate measurements cannot be made in the transistion zone.

Another problem with many prior art urine collection systems is that they employ a large volume collection bag as a separate element with respect to a metering chamber and are interconnected with the chamber by means of a flexible tube. Such a structure has been found cumbersome to use and transport when filled and is subject to accidental separation.

In addition to overcoming the above described disadvantages with present day urine collection systems, it is also desirable to provide a metering and collection system which enables the sampling of urine directly from the metering chamber.

Accordingly, it is an objective of this invention to provide a closed, combined urine collection and metering system of improved structural rigidity and which provides relatively accurate metering of small and large volumes with a smooth transistion between the small and large portions of the metering chamber.

It is another objective of this invention to provide an improved urine collection and metering system which is relatively inexpensive and easy to manufacture and use and which functions as a closed system collection bag when accurate metering of urine output is not required.

Additional objectives and advantages of this invention will be set forth in part in the description which follows, and in part will be obvious from the description, or may be learned by practice of the invention. The objectives and advantages of this invention may be realized and attained by means of the instrumentalities and combinations particularly pointed out in the appended claims.

BRIEF DESCRIPTION OF THE INVENTION to achieve the foregoing objectives and in accordance with the purpose of this invention, as embodied and broadly described herein, the urine metering and collection system of this invention comprises a stiff integral head member including a closed volume calibrated chamber having a front wall with calibrations, a rear wall, a top wall, a bottom wall, and first and second sidewalls. At least the section of the front wall having calibrations thereon or adjacent thereto is transparent and the sidewalls are provided which continuously converge downwardly toward each other throughout at least a major portion of the length of the chamber such that each horizontal section of the chamber within the major portion has a smaller volume per unit of height than does the next adjacent upper section of the chamber.

An outlet passageway is provided through the bottom wall or one of the sidewalls at a location adjacent the bottom wall. The head member also includes an inlet passageway communicating with the chamber adjacent to the top thereof, an overflow passageway with one end being in fluid-flow communication with the top of the chamber and an air vent in air-flow communication with the chamber.

A tube is attached at one end to the head member and in fluid-flow communication with the inlet passageway and has its other end adapted for connection to a catheter. A collection bag is provided which has a first opening in fluid-flow communication with the other end of the overflow passageway, and a second opening in fluid-flow communication with the outlet passageway.

Preferably the head member is formed of two unitary sheets formed to provide various elements of the head member and being sealed together along the top and sides of the head member, the bottom of the sheets being sealed to the top of the collection bag.

In another embodiment conduit means are provided for placing the chamber outlet passageway in fluid-flow communication with the second opening in the collection bag, the conduit means having a sampling outlet and a valve having three operative positions, a first position for obturating the conduit means, a second position for enabling flow from the chamber to the bag and a third position for enabling flow from the chamber to the sampling outlet.

The invention consists in the novel parts, constructions, arrangements, combinations and the improvements shown and described. The accompanying drawings, which are incorporated in and constitute a part of the specification, illustrate one embodiment of the invention and together with the description, serve to explain the principles of the invention.

DESCRIPTION OF ONE EMBODIMENT OF THE INVENTION

Reference will now be made in detail to the preferred embodiment of this invention, an example of which is illustrated in the accompanying drawings.

Figure 1:
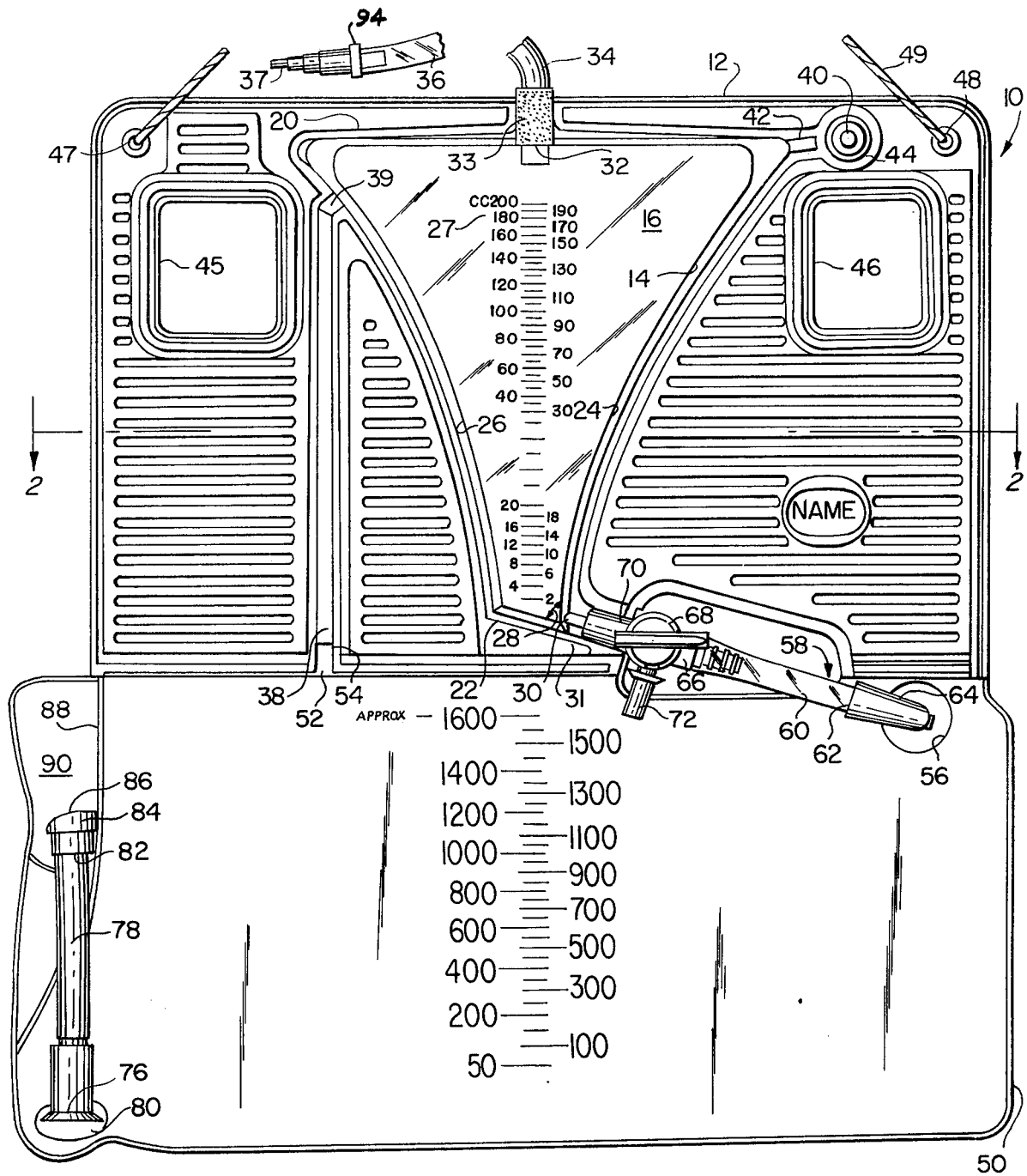
FIG. 1 is a front elevational view of a urine metering and collection system formed in accordance with this invention.

Throughout the specification and claims terms of orientation, such as up and down, bottom and top, front and back are used with respect to the orientation of the system as shown in FIG. 1 and as exists during use thereof. These terms are not intended to be limiting but are used for convenience, simplicity and clarity of description.

In accordance with this invention, the urine metering and collection system 10 includes a relatively stiff or rigid integral head member and a collection bag secured to the bottom of the head member. As used throughout this specification and the claims, the terms stiff and rigid indicate a nonpliant degree of flexibility and are not intended to require inflexibility. As here embodied a head member 12 is formed with a volume calibrated chamber 14 having a front wall 16, a rear wall 18, a top wall 20, a bottom wall 22 and first and second sidewalls 24, 26 respectively. The sidewalls 24, 26 continuously converge towards each other and preferably are formed with a continuous curvature which is concave with respect to the interior of the chamber 14. As can be seen in FIG. 1, the walls are formed with approximately a hyperbolic curvature wherein each horizontal section of the chamber 14 has a smaller volume per unit of height than does the next adjacent upper section of the chamber. In other words, the volume per unit height smoothly and gradually increases from the bottom of the chamber toward the top of the chamber for at least the major portion of the length of the chamber. Volumetric calibrations 27 are marked on the front wall 16. At least the portion of the front wall 16 on which the calibrations are printed, or adjacent thereto, is transparent to permit viewing the liquid level in the metering chamber 14.

Preferably, the bottom wall 22 slopes downwardly forming an acute angle 28 with the first wall 24. This downward slope of the bottom wall 22 causes the urine to be gravity fed to the lowest point of the chamber 14 which is helpful during drainage as well as providing accurate measurements at very small volumes. An outlet port 30 is provided at the position of lowest location of the chamber 14. The outlet port 30 can be provided through the bottom wall 22 or through the first sidewall 24 adjacent to the bottom wall 22. In the embodiment shown in FIG. 1, an outlet port 30 and passageway 31 are formed through the sidewall 24 and are adapted to receive a conduit means as described below.

The head member 12 is also formed with an inlet port 32 and passageway 33 preferably through the top wall 20 of the chamber 14. The inlet port passageway 33 is adapted to receive a flexible tube 34 which is provided at its remote end 36 with a conventional connection 37 adapted to be attached to a catheter (not shown) such as a Foley catheter.

The head member 12 is also formed with an overflow passageway 38 one end 39 of which connects with the upper portion of the chamber 14 for fluid-flow communication with the interior of the chamber. An air vent 40 is formed in the head member 12 which vents the chamber 14 to the atmosphere through air vent passageway 42. Preferably a microbiological filter 44 is inserted in the air vent in order to permit the passage of air but prevent the passage of liquid and bacteria. Suitable filters are commercially available such as Pallflex and Milipore filters.

Hand holes 45, 46 are provided through the head member 12 to facilitate carrying the metering and collection system 10. Hanger holes 47, 48 are provided at opposite ends of the head member adjacent to the upper edge to receive a hanger 49 such as a nylon cord to permit suspending the system 10 such as from a hook (not shown).

In accordance with this invention, a collection bag 50 is provided which, preferably, is fixedly secured to the head member 12 below the metering chamber 14. In one embodiment the collection bag 50 is attached to the bottom of the head member 12 and is provided with a first opening 52 near the top of the bag which is adapted to be sealed to and receive the bottom end 54 of the overflow passageway 38. This permits the overflow passageway 38, together with the top of the chamber 14 and the air vent 40 to serve as an air vent for the collection bag 50.

A second opening 56 is provided near the top of the bag 50 adapted to receive conduit means 58 for placing the chamber 14 and the bag 50 in fluidflow communication. The conduit means 58 includes a tube, such as a flexible polyvinylchloride tube 60 attached to the bag 50 at one end 62 by means of a right angle tube and flange connector 64. The other end of the tube 60 may be attached directly to the metering chamber outlet passageway 39 but preferably is attached to one outlet 66 of a valve 68. The valve 68 is also provided with a second outlet 70 connected to the outlet passageway 31 of the metering chamber 14. The valve 68 may be provided with a third outlet 72 which is adapted to be connected to external tubing (not shown) for purposes of sampling urine collected in the metering chamber 14. Each of these connections are firm and hermetically sealed and can be accomplished by thermal or solvent welding. When it is desired to include easy sampling capability to the system a threeway valve 68 is provided which in one position obturates the sampling outlet 72 and the outlet 66 leading to the collection bag 50 thereby isolating the metering chamber 14 from the collection bag 50 except by means of the overflow tube 40. In the second position of the valve 68 fluid is permitted to flow from the metering chamber 14 directly to the collection bag 50 and the sampling port 72 is closed. In the third position fluid is permitted to flow from the metering chamber 14 through the sampling port 72 and the port 66 leading to the collection bag 50 is closed.

Further in accordance with this invention, the collection bag 50 may be provided with a third opening 76 adjacent to one of the bottom corners of the bag and a drain tube 78 is connected to the opening 76 through a tubing and flange connector 80. The distal end 82 of the drain tube 78 has a closure cap 84 placed thereon and is adapted to be inserted into a pocket 86 formed in the bag 50. The opposing walls of the bag 50 are sealed together by a seam 88 which seals the majority of the bag 50 from that portion 90 of the bag which includes the pocket 86 so that any urine collected in the bag 50 cannot flow into the portion of the bag 90 which includes the pocket 86. The pocket merely serves as a convenient retainer for the drain tube 78 when the drain tube is not in use.

Figure 2:
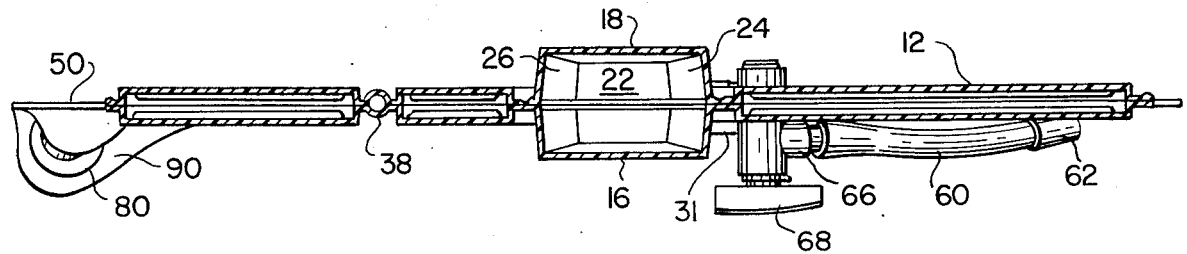
FIG. 2 is a sectional view taken along line 2—2 of FIG. 1.

The head member 12 is preferably formed of a relatively rigid moldable plastic. It has been found that a suitable plastic for this system is polyvinylchloride. In accordance with one embodiment of this invention the head is formed of two sheets, which may be vacuum molded such that the metering chamber 14, overflow passageway 38, air vent 40, outlet port passageway 31 and inlet port passageway 33 are integrally formed as a part of the head member 12. As can be more easily seen from the sectional view of FIG. 2 in one form of head member these passageways and chamber are formed with half of each being molded into each sheet so that when the sheets are joined, such as by solvent or thermal welding, the complete passageway is formed. In another form the passageway and chamber can be formed in one of the sheets with the other sheet completing these portions and providing a planar back surface. The head member 12, as part of the vacuum forming procedure, can also be provided with integral ribs to provide structural rigidity. Preferably the polyvinylchloride used for the head member 12 is transparent, at least in the section of the front wall 16 of the metering chamber 14 immediately adjacent the volume calibrations 27.

The collection bag 50 is formed of two die cut sheets of flexible material such as polyvinylchloride with at least the front face thereof being transparent so that by calibrating the front face of the collection bag 50, rough estimations of large volume collection can be made by comparing the fluid surface line with the calibrations.

In a preferred embodiment of this invention, the sheets forming the head member 12 are heat sealed together along the top and sides of the head member, along the periphery of the metering chamber 14, along the length of each of the passageways and along the periphery of the air vent 40. This ensures that all areas which receive and are exposed to the urine are sealed against leakage and exposure to the atmosphere. The bottom of the head member 12 receives and is sealed to the top of the collection bag 50 thereby completing the seal of the head member 12 and contemporaneously sealing the collection bag 50. The remainder of the periphery of the collection bag is heat sealed. It has been found that high frequency welding satisfactorily joins the rigid polyvinylchloride head member 12 to the flexible polyvinylchloride bag 50.

In operation, the connection 37 of the drainage tube 34 is attached to a catheter and the metering and collection system 10 of this invention is mounted, such as by hanging, onto the bed of the patient being monitored. When metering of the volume flow is desired, the valve 68 is positioned so that the metering chamber 14 is isolated from the collection bag 50 except through the overflow passageway 38. As the urine collects within the metering chamber 14 its volume can be easily read on the calibration scale on the front wall 16 of the metering chamber 14. If it is desired to sample the urine collected within the metering chamber 14 for chemical or physical analysis, the valve 68 is placed in its third position so that a sample may be extracted through the sampling port 72. In the event that the volume of urine produced exceeds the expected production and the valve 68 is in its first or closed position, any excess urine flows through the overflow passageway 38 into the collection bag 50.

After metering is accomplished for a predetermined period of time the valve 68 is opened manually to permit the collected urine to flow from the metering chamber 14 into the collection bag 50 were additional approximate metering can be accomplished by the calibration scale on the front face of the collection bag 50. When it is desired to empty the collection bag 50, the distal end 82 of the drain tube 78 is removed from the pocket 86 and the closure cap 84 is removed from the distal end 82 permitting emptying the collection bag into an appropriate dispensing location.

In accordance with another feature of the preferred embodiment of this invention, a self sealing valve is provided upstream of the head member 12 to facilitate the taking of a sterile sample as close to the catheter without puncturing the catheter wall with a needle. As here embodied, such a valve 94 is incorporated as part of the catheter connector 37, although the self sealing valve 94 could be included in the tube 34 connecting the catheter with the head member 12. The valve 94 does not interfere with flow from the catheter to the head member 12 through the tube 34 but permits samples to be removed as soon as the urine leaves the catheter. Suitable self sealing valves are commercially available, such as a latex diaphragm or a valve commercially known as a Halkey Roberts No. 2049 valve.

In order to remove a sterile sample, a syringe is inserted into the self sealing valve 94 and the syringe plunger is retracted to effect containment of the sample in the syringe. The syringe then is removed and the valve seals automatically.

As can be seen from the above description taken with the drawing, the urine metering and collection system of this invention provides a single integral, in-line, closed metering and collection system which is rigid in its construction, which cannot accidentally separate, and which may be made easily and inexpensively by virtue of the fact that most of the system is vacuum molded, die cut and welded together. The particular curvature of the sides of the metering chamber 14 provide continuous, gradual increase in volume which facilitates accurate reading of the volume within the metering chamber at small volume quantities and large volume quantities without any discontinuity between the two.

What is claimed as new and desired to be secured by Letters Patent of the U.S. is:

1. A urine metering and collection system comprising:
  a. a stiff head member including a closed volume calibrated chamber having a substantially flat front wall, a substantially flat rear wall, a top wall, and first and second sidewalls, a bottom wall sloping downwardly and forming an acute angle with said first sidewall, one of said walls having volumetric calibrations thereon, at least a section of said one of said walls having the calibrations thereon or adjacent thereto being transparent, the sidewalls continuously converging downwardly toward each other throughout at least a major portion of the length of said chamber such that each horizontal section of the chamber within said major portion has a smaller volume per unit of height than does the next adjacent upper horizontal section of the chamber, an outlet passageway at the bottom of said chamber through said first sidewall and in alignment with said bottom wall, an inlet passageway communicating with the chamber adjacent to the top of the chamber, an overflow passageway having one end in fluid-flow communication with said chamber adjacent to the top thereof and an air vent in air-flow communication with said chamber;
  b. an inlet tube attached at one end to said head member and in fluid-flow communication with said inlet passageway, the other end of said inlet tube being adapted for connection to a catheter; and
  c. a collection bag fixedly secured to the head member below said chamber and having a first opening in fluid-flow communication with the other end of said overflow passageway, and a second opening in fluid-flow communication with said outlet passageway.

2. A urine metering and collection system comprising:
  a. a stiff head member including a closed volume calibrated chamber having a substantially flat front wall, a substantially flat rear wall, a top wall, and first and second sidewalls, one of said walls having volumetric calibrations thereon, at least a section of said one of said walls having the calibrations thereon or adjacent thereto being transparent, the sidewalls continuously converging downwardly towards each other throughout at least a major portion of the length of chamber such that each horizontal section of the chamber within said major portion has a smaller volume per unit of height than does the next adjacent upper horizontal section of the chamber, an outlet passageway at the bottom of said chamber, an inlet passageway communicating with the chamber adjacent to the top of the chamber, an overflow passageway formed as an integral part of said head member and having one end in fluid-flow communication with said chamber adjacent to the top thereof and an air vent in air-flow communication with said chamber, said head member being formed of two unitary plastic sheets molded to form said chamber, said outlet passageway, said overflow passageway and said air vent, said sheets being sealed together along the perimeter thereof, along the periphery of the chamber, along the length of said overflow passageway, and along the periphery of the air vent and the outlet passageway;

b. an inlet tube attached at one end to said head member and in fluid-flow communication with said inlet passageway, the other end of said inlet tube being adapted for connection to a catheter; and c. a collection bag fixedly secured to the head member below said chamber and having a first opening in fluid-flow communication with the other end of said overflow passageway, and a second opening in fluid-flow communication with said outlet passageway.

3. The system of claim 1 including conduit means for placing the chamber outlet passageway in fluid-flow communication with said second opening, said conduit means having a sampling outlet, a valve in said conduit means, said valve having three operative positions, a first position obturating said conduit means and preventing flow from said chamber to said bag and said sampling outlet, a second position enabling flow from said chamber to said bag and preventing flow to said sampling outlet, and a third position preventing flow from said chamber to said bag and enabling flow from said chamber to said sampling outlet.

4. The system of claim 3 wherein said conduit means is hermetically sealed at one end to said outlet passageway and hermetically sealed at its other end to said second opening.

5. The system of claim 1 wherein said overflow passageway is formed as an integral part of the head member and where said head member is formed of two unitary sheets sealed together to form said chamber, said outlet passageway, said inlet passageway, said overflow passageway and said air vent, said sheets being sealed together along the top and sides thereof, the bottom of said sheets being sealed to the top of the collection bag and the top of the collection bag being sealed closed except for said first opening.

6. The system of claim 2 wherein the bottom wall of said chamber slopes downwardly forming an acute angle with said first sidewall and wherein said outlet passageway is through said first sidewall and in alignment with said bottom wall.

7. The system of claim 1 including a third opening near the bottom of said bag, a drain tube in fluid-flow communication with the third opening and means for obturating the drain tube.

8. The system of claim 2 wherein the sidewalls have a continuous curvature concave relative to the interior of the chamber.

9. The system of claim 1 including a self-sealing valve mounted adjacent to said other end of the inlet tube.

10. The system of claim 2 including a self-sealing valve mounted adjacent to said other end of the inlet tube.

* * * * *